United States Patent
Yamazaki et al.

(10) Patent No.: US 12,396,911 B2
(45) Date of Patent: Aug. 26, 2025

(54) WALKING TRAINING SYSTEM, OPERATION METHOD OF THE SYSTEM, AND NON-TRANSITORY STORAGE MEDIUM FOR THE SYSTEM

(71) Applicant: TOYOTA JIDOSHA KABUSHIKI KAISHA, Toyota (JP)

(72) Inventors: Seisuke Yamazaki, Toyota (JP); Takashi Tomoto, Miyoshi (JP); Yoshimasa Ito, Ichinomiya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 799 days.

(21) Appl. No.: 17/724,674

(22) Filed: Apr. 20, 2022

(65) Prior Publication Data
US 2022/0362091 A1    Nov. 17, 2022

(30) Foreign Application Priority Data
May 12, 2021    (JP) .................... 2021-081118

(51) Int. Cl.
*A61H 1/02*    (2006.01)
*A61B 5/00*    (2006.01)
*A61B 5/11*    (2006.01)
*A63B 22/02*    (2006.01)

(52) U.S. Cl.
CPC ............ *A61H 1/0262* (2013.01); *A61B 5/112* (2013.01); *A61B 5/4836* (2013.01); *A63B 22/02* (2013.01)

(58) Field of Classification Search
CPC ................. B25J 9/0006; A61H 1/0262; A61H 1/0237–0259; A61H 2001/0248–0251; A61H 3/00
See application file for complete search history.

(56) References Cited

U.S. PATENT DOCUMENTS

| | | | |
|---|---|---|---|
| 11,311,447 B2 * | 4/2022 | Gordon | A63B 22/02 |
| 2015/0342819 A1 * | 12/2015 | Shimada | A63B 21/4011 623/27 |
| 2016/0166460 A1 | 6/2016 | Murphy et al. | |
| 2017/0027803 A1 * | 2/2017 | Agrawal | A61B 5/1122 |

FOREIGN PATENT DOCUMENTS

| | | | |
|---|---|---|---|
| JP | 2019-118706 A | | 7/2019 |
| KR | 20170143276 A | * | 6/2016 |
| KR | 10-2017-0143276 A | | 12/2017 |

* cited by examiner

*Primary Examiner* — Kendra D Carter
*Assistant Examiner* — Jaeick Jang
(74) *Attorney, Agent, or Firm* — Oliff PLC (57) ABSTRACT

A walking training system includes a leg orthosis fitted to a leg of a user, a pulling member coupled to the leg orthosis, a first drive mechanism configured to apply pull force to the pulling member, according to walking motion of the user, a holding device that holds the pulling member at a holding level, at a point between a coupling point of the leg orthosis and the first drive mechanism, and a second drive mechanism configured to change the holding level of the pulling member held by the holding device, according to the walking motion of the user.

11 Claims, 10 Drawing Sheets

WALKING TRAINING SYSTEM, OPERATION METHOD OF THE SYSTEM, AND NON-TRANSITORY STORAGE MEDIUM FOR THE SYSTEM

CROSS-REFERENCE TO RELATED APPLICATION

This application claims priority to Japanese Patent Application No. 2021-081118 filed on May 12, 2021, incorporated herein by reference in its entirety.

BACKGROUND

1. Technical Field

The disclosure relates to a walking training system, an operation method of the system, and a non-transitory storage medium for the system.

2. Description of Related Art

An example of a walking training apparatus is disclosed in Japanese Unexamined Patent Application Publication No. 2019-118706 (JP 2019-118706 A).

SUMMARY

In the walking training apparatus, a leg orthosis may be fitted to a leg of a user, such as a rehabilitation patient. In the apparatus described in JP 2019-118706 A, the leg orthosis includes a motor that generates driving force for assisting in extension motion and flexion motion of the knee joint. As the driving force of the motor is increased, the weight of the leg orthosis increases. As a result, an increased load is imposed on the trainee (user), which makes it difficult for the trainee to conduct training appropriately. Further, this may make wearing of the leg orthosis cumbersome and complicated.

The disclosure provides a walking training system with which walking training is performed appropriately, and an operation method of the walking training system.

A walking training system according to a first aspect of the disclosure includes a leg orthosis fitted to a leg of a user, at least one pulling member coupled to the leg orthosis, a first drive mechanism configured to apply pull force to the pulling member, according to a walking motion of the user, a holding device that holds the pulling member at a holding level, at a point between a coupling point of the leg orthosis and the first drive mechanism, and a second drive mechanism configured to change the holding level of the pulling member held by the holding device, according to the walking motion of the user.

The leg orthosis may have a joint mechanism configured to pivot according to the walking motion of the user, and the first drive mechanism may be configured to pivot the joint mechanism, by pulling the pulling member.

In the above walking training system, the pulling member may be coupled to the leg orthosis from ahead of the user, and the first drive mechanism may be configured to provide the pull force, by reeling in the pulling member.

In the above walking training system, the holding device may have a suspended member that is suspended from above the user, and the second drive mechanism may be configured to raise the holding level, by reeling in the suspended member.

The holding device may have a support member that extends upward, and the second drive mechanism may be configured to change the holding level, by extending and contracting the support member.

In the above walking training system, the at least one pulling member may be a plurality of pulling members, and the plurality of pulling members may be connected to the leg orthosis from different directions.

In the above walking training system, the pulling member may be coupled to the leg orthosis from one side of the user, and the leg orthosis may be provided with a mechanism configured to change a direction of the pull force of the pulling member.

An operation method of a walking training system according to a second aspect of the disclosure is that of the walking training system including a leg orthosis fitted to a leg of a user, at least one pulling member coupled to the leg orthosis, a first drive mechanism configured to apply pull force to the pulling member, a holding device that holds the pulling member at a holding level, at a point between a coupling point of the leg orthosis and the first drive mechanism, and a second drive mechanism configured to change the holding level of the pulling member held by the holding device. The operation method includes detecting a walking motion of the user, and controlling the first drive mechanism and the second drive mechanism according to the walking motion of the user.

In the above operation method, the leg orthosis may have a joint mechanism configured to pivot according to the walking motion of the user, and the first drive mechanism may pivot the joint mechanism, by pulling the pulling member.

In the above operation method, the pulling member may be coupled to the leg orthosis from ahead of the user, and the first drive mechanism may provide the pull force, by reeling in the pulling member.

In the above operation method, the holding device may have a suspended member that is suspended from above the user, and the second drive mechanism may raise the holding level, by reeling in the suspended member.

In the above operation method, the holding device may have a support member that extends upward, and the second drive mechanism may change the holding level, by extending and contracting the support member.

In the above operation method, the at least one pulling member may be a plurality of pulling members, and the plurality of pulling members may be connected to the leg orthosis from different directions.

In the above operation method, the pulling member may be coupled to the leg orthosis from one side of the user, and the leg orthosis may be provided with a mechanism configured to change a direction of the pull force of the pulling member.

A third aspect of the disclosure relates to a non-transitory storage medium for a walking training system. The walking training system includes a leg orthosis fitted to a leg of a user, at least one pulling member coupled to the leg orthosis, a first drive mechanism configured to apply pull force to the pulling member, a holding device that holds the pulling member at a holding level, at a point between a coupling point of the leg orthosis and the first drive mechanism, and a second drive mechanism configured to change the holding level of the pulling member held by the holding device. The non-transitory storage medium stores instructions that are executable by one or more processors and that cause the one or more processors to perform functions comprising:
 detecting a walking motion of the user; and controlling the first drive mechanism and the second drive mechanism by the controller, according to the walking motion of the user.

According to the disclosure, the walking training system with which walking training is performed appropriately, and the operation method of the system, are provided.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

While the disclosure will be described through one embodiment of the disclosure, the disclosure will not be limited to the following embodiment. Also, not all of the configurations that will be described in the embodiment are necessarily essential as devices for solving the above problems.

First Embodiment

Figure 1:
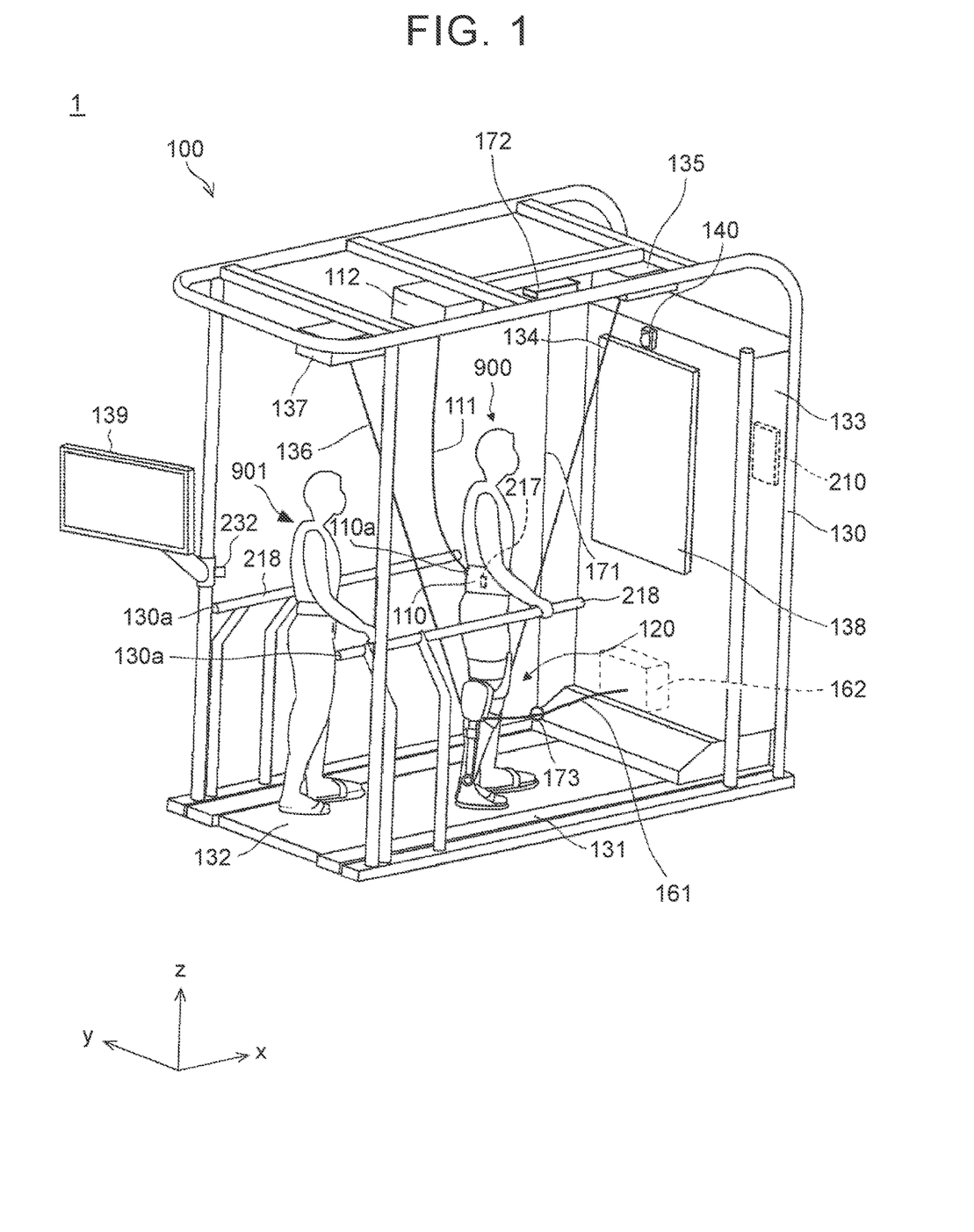
FIG. 1 is a schematic perspective view of a walking training system according to one embodiment.

A first embodiment will be described with reference to the drawings. FIG. 1 shows one example of the configuration of a rehabilitation support system according to the first embodiment. The rehabilitation support system (walking training system 1) according to this embodiment principally consists of a walking training apparatus 100 and a leg orthosis 120. In the following description, an XYZ three-dimensional Cartesian coordinate system will be used as needed. In the coordinate system, the X direction is a direction in which a trainee 900 walks, and the Y direction is the lateral direction of the trainee 900, while the Z direction is the vertical direction. Namely, the +X direction is forward of the trainee 900 who is undergoing walking training, and the −X direction is rearward of the trainee 900. Similarly, the +Y direction is the left direction, and the −Y direction is the right direction, while the +Z direction is the upward direction, and the −Z direction is the downward direction, with respect to the trainee 900 in walking training.

The walking training apparatus 100 is one specific example of a rehabilitation support apparatus that assists the trainee (user) 900 in rehabilitation. The walking training apparatus 100 is used by the trainee 900, who is a hemiplegic patient suffering paralysis in one leg, when he/she performs walking training under the guidance of a trainer 901. Here, the trainer 901 may be a therapist (physical therapist) or a physician, and may also be called "training guide", "training helper", or "training assistant" as the trainer 901 helps the trainee with training through guidance or assistance, for example.

The walking training apparatus 100 mainly includes a control panel 133 mounted to a frame 130 that forms the overall framework, a treadmill 131 on which the trainee 900 walks, and the leg orthosis 120 fitted to an impaired leg as a paralyzed leg of the trainee 900. In FIG. 1, the leg orthosis 120 is fitted to the right leg of the trainee 900.

The frame 130 is erected on the treadmill 131 installed on a floor. The treadmill 131 rotates a ring-shaped belt 132 by means of a motor (not shown). The treadmill 131 promotes the trainee 900 to walk, and the trainee 900 who conducts walking training steps on the belt 132, and tries walking motion in accordance with movement of the belt 132. While the trainer 901 can walk together with the trainee 900 while standing on the belt 132 behind the trainee 900, as shown in FIG. 1 by way of example, it is generally preferable that the trainer 901 is in a condition, like standing across the belt 132, where he/she can easily help the trainee 900.

The frame 130 supports the control panel 133 that houses an overall controller 210 that controls motors and sensors, a monitor for training 138, such as a liquid crystal panel, which presents the progress of training, etc. to the trainee 900, and so forth. The frame 130 also supports an anterior pulling portion 135 located above and anterior to the head of the trainee 900, a harness pulling portion 112 located above the head, and a posterior pulling portion 137 located above and posterior to the head. Also, the frame 130 includes handrails 130a which allow the trainee 900 to grab or hold.

The handrails 130a are arranged on the right and left sides of the trainee 900. Each of the handrails 130a is disposed in parallel with the walking direction of the trainee 900. The vertical and lateral positions of the handrails 130a can be adjusted. Namely, the handrails 130a may include a mechanism for changing their height and width. Further, the handrail 130a may be constructed such that its inclination angle can be changed, by adjusting the height so that it varies between the front side and the rear side in the walking direction, for example. For example, the handrail 130a may be formed with the inclination angle that gradually makes the handrail 130a higher along the walking direction.

Also, the handrail 130a is provided with a handrail sensor 218 that detects a load received from the trainee 900. For example, the handrail sensor 218 may be a load detection sheet of a resistance change detection type in which electrodes are arranged in a matrix. Also, the handrail sensor 218 may be a six-axis sensor as a composite of a three-axis acceleration sensor (x, y, z) and a three-axis gyro sensor (roll, pitch, yaw). It is, however, to be understood that the handrail sensor 218 may be of any type, and may be installed at any position.

A camera 140 functions as an image pickup unit for observing the whole body of the trainee 900. The camera 140 is installed in the vicinity of the monitor for training 138, to be opposed to the trainee. The camera 140 captures still images and moving images of the trainee 900 in training. The camera 140 includes a set of lens and image pickup device, which provides an angle of view large enough to shoot the whole body of the trainee 900. The image pickup device may be a CMOS (Complementary Metal-Oxide-Semiconductor) image sensor, for example, which converts an optical image formed on an imaging plane into an image signal.

Through coordinated movements of the anterior pulling portion 135 and the posterior pulling portion 137, the load of the leg orthosis 120 is cancelled so as not to be a burden on the impaired leg, and, further, swing motion of the impaired leg is assisted according to the degree of settings.

An anterior wire 134 is coupled at one end to a take-up mechanism of the anterior pulling portion 135, and is coupled at the other end to the leg orthosis 120. The take-up mechanism of the anterior pulling portion 135 has a motor (not shown), and reels in or reels out the anterior wire 134 in accordance with movement of the impaired leg, by turning on/off the motor. Similarly, a posterior wire 136 is coupled at one end to a take-up mechanism of the posterior pulling portion 137, and is coupled at the other end to the leg orthosis 120. The take-up mechanism of the posterior pulling portion 137 has a motor (not shown), and reels in or reels out the posterior wire 136 in accordance with movement of the impaired leg, by turning on/off the motor. Through the coordinated movements of the anterior pulling portion 135 and the posterior pulling portion 137, the load of the leg orthosis 120 is cancelled, so as not to become a burden on the impaired leg, and the swing motion of the impaired leg is assisted according to the degree of settings.

For example, the trainer 901, as an operator, sets the level of assistance to a high level, for a trainee suffering a severe paralysis. When the level of assistance is set to a high level, the anterior pulling portion 135 reels in the anterior wire 134 with a relatively large force, in accordance with the swing timing of the impaired leg. As the training proceeds, and the trainee does not need assistance, the trainer 901 sets the level of assistance to a minimum. When the level of assistance is set to the minimum, the anterior pulling portion 135 reels in the anterior wire 134 with force that only cancels the self-weight of the leg orthosis 120, in accordance with the swing timing of the impaired leg.

The walking training apparatus 100 includes a fall-prevention harness device as a safety device, which principally consists of an orthosis 110, a harness wire 111, and a harness pulling portion 112. The orthosis 110 is a belt that is wrapped around the abdomen of the trainee 900 and secured to the waist with a hook-and-loop fastener, for example. The orthosis 110 includes a connection hook 110a to which one end of the harness wire 111 as a hanging member is coupled, and may also be called "hanger belt". The trainee 900 wears the orthosis 110, such that the connection hook 110a is located on the back region.

The harness wire 111 is coupled at one end to the connection hook 110a of the orthosis 110, and is coupled at the other end to a take-up mechanism of the harness pulling portion 112. The take-up mechanism of the harness pulling portion 112 has a motor (not shown), and reels in or reels out the harness wire 111, by turning on/off the motor. With this arrangement, when the trainee 900 is about to fall, the fall-prevention harness device reels in the harness wire 111 according to a command of the overall controller 210 that detects the movement of the trainee 900, and causes the orthosis 110 to support the upper body of the trainee 900, so as to prevent the trainee 900 from falling.

The orthosis 110 includes a posture sensor 217 for detecting the posture of the trainee 900. The posture sensor 217 is a combination of a gyro sensor and an acceleration sensor, for example, and outputs the inclination angle of the abdomen to which the orthosis 110 is fitted, relative to the direction of the gravity.

The monitor for management 139, which is attached to the frame 130, is a display input device used mainly by the trainer 901 for monitoring and operation. The monitor for management 139 is a liquid crystal panel, for example, and a touch panel is provided on a surface of the monitor for management 139. The monitor for management 139 displays various menu items concerning training settings, various parameters for use in training, training results, and so forth. Also, an emergency stop button 232 is provided in the vicinity of the monitor for management 139. When the trainer 901 pushes the emergency stop button 232, the walking training apparatus 100 makes an emergency stop.

The leg orthosis 120 is fitted to the impaired leg of the trainee 900, and assist the trainee 900 in walking, by reducing a load of extension and flexion at the knee joint of the impaired leg. The leg orthosis 120 may include a sensor that measures a load at the sole, and so forth, and output various kinds of data concerning leg movements to the overall controller 210. The leg orthosis 120 will be described in detail later.

A wire 161 is connected to the leg orthosis 120. The wire 161 is connected to a first drive mechanism 162. The first drive mechanism 162 applies pull force to the wire 161, according to the walking motion of the trainee 900. The first drive mechanism 162 has a motor and a take-up mechanism for applying the pull force to the wire 161. Namely, the first drive mechanism 162 reels in or reels out the wire 161, by driving the motor. The wire 161 is attached at one end to the leg orthosis 120, and is attached at the other end to the first drive mechanism 162. The wire 161 is pulled around at a level around the knee height of the trainee 900. The wire 161 is pulled around horizontally.

The first drive mechanism 162 is located ahead of the trainee 900. For example, the first drive mechanism 162 is housed in the control panel 133 located ahead of the treadmill 131. The wire 161 is connected from ahead of the trainee 900 to the leg orthosis 120. In operation, the first drive mechanism 162 can apply pull force to the leg orthosis 120, by reeling in the wire 161. The first drive mechanism 162 can weaken the pull force applied to the leg orthosis 120, by reeling out the wire 161. In this manner, a joint portion of the leg orthosis 120 is driven. In other words, the first drive mechanism 162 drives the wire 161, so that the angle of the joint portion of the leg orthosis 120 becomes equal to a desired angle.

A holding belt 171 is connected to the wire 161 at a point on the wire 161. The holding belt 171 is located so as not to interfere with the trainee 900 in walking motion. For example, the holding belt 171 is located ahead of the trainee 900. The holding belt 171 and the wire 161 are connected via a connecting portion 173. For example, the holding belt 171 is wound around the wire 161, so that the lower end of the holding belt 171 is attached to the wire 161. The connecting portion 173 is a connection position at which the holding belt 171 and the wire 161 are connected to each other. The connection position of the holding belt 171 on the wire 161 may be fixed. The holding belt 171 provides a holding device that holds the wire 161 at a given level. The connecting portion 173 may have a coupling member, such as a ring or a hook. Namely, the holding belt 171 holds the wire 161 at the given level.

Further, the holding belt 171 is connected to a second drive mechanism 172. The second drive mechanism 172 is fixed to the frame 130, at above the trainee 900. The second drive mechanism 172 has a motor and a take-up mechanism for applying pull force to the holding belt 171. The holding belt 171 is attached at the lower end to the connecting portion 173, and is attached at the upper end to the second drive mechanism 172. The holding belt 171 is suspended from the upper frame 130 down to the connecting portion 173. The holding belt 171 is connected to the wire 161 at the connecting portion 173.

The second drive mechanism 172 reels in or reels out the holding belt 171, so that the connecting portion 173 moves up and down. Accordingly, the level of the wire 161 is changed. The second drive mechanism 172 changes the holding level of the wire 161. Namely, the second drive mechanism 172 drives the holding belt 171, so that the level of the wire 161 becomes equal to a desired level. In this manner, the pulling direction of the wire 161 can be changed.

The overall controller 210 generates rehabilitation data that may include configuration parameters concerning training settings, various kinds of data concerning leg movements generated from various sensors as training results, and so forth. The rehabilitation data may include data indicating the trainer 901, or his/her years of experience, level of proficiency, or the like, data indicating the symptoms, walking ability, degree of recovery, etc., of the trainee 900, and various kinds of data transmitted from sensors, etc. The overall controller 210 generates a control signal for controlling each drive unit. The overall controller 210 controls each drive unit, based on detection signals from various sensors. Thus, it is possible to appropriately control the pull force and the take-up length, in accordance with the walking motion of the trainee 900.

Figure 2:
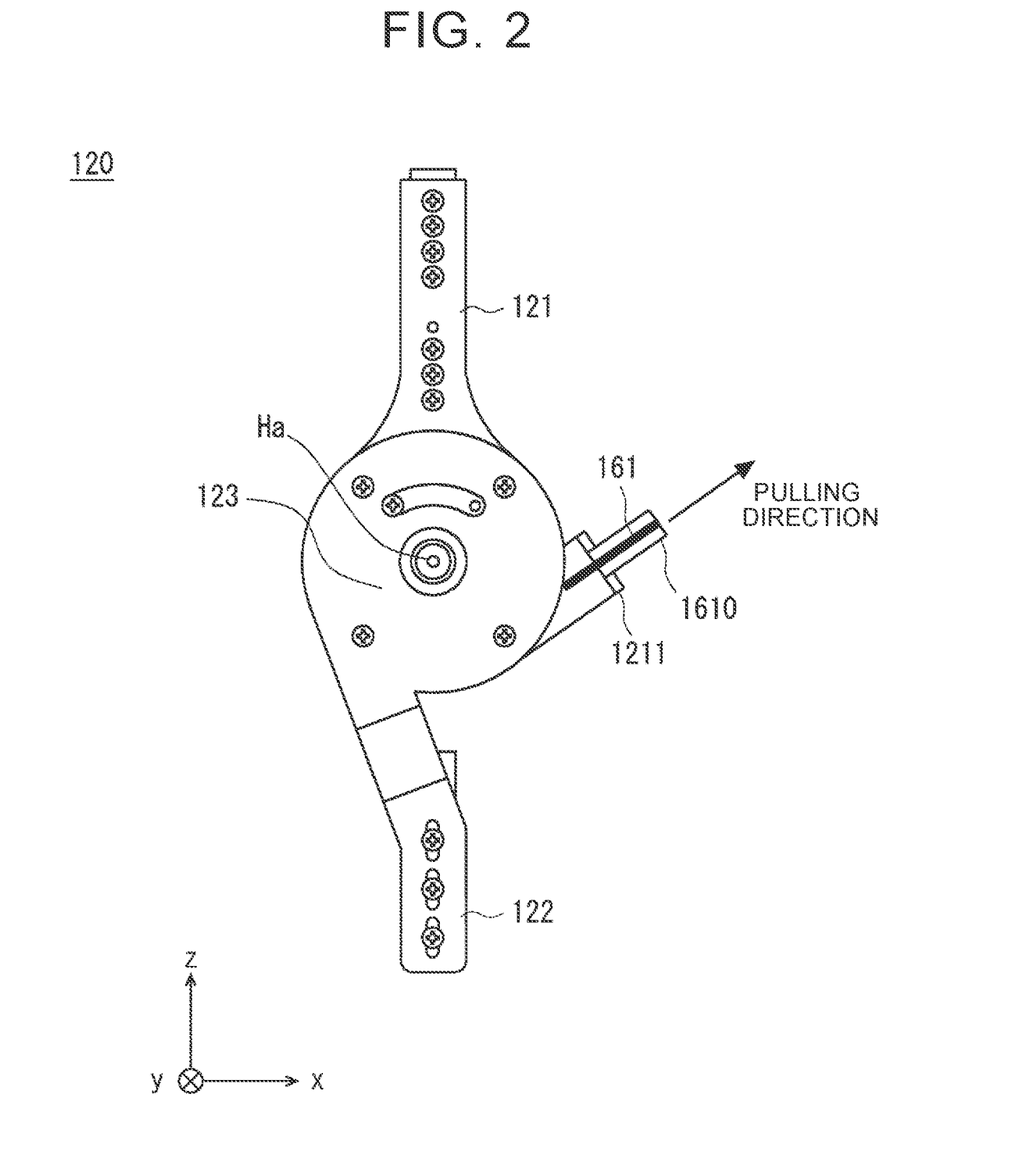
FIG. 2 is a side view showing the configuration of a leg orthosis.
Figure 3:
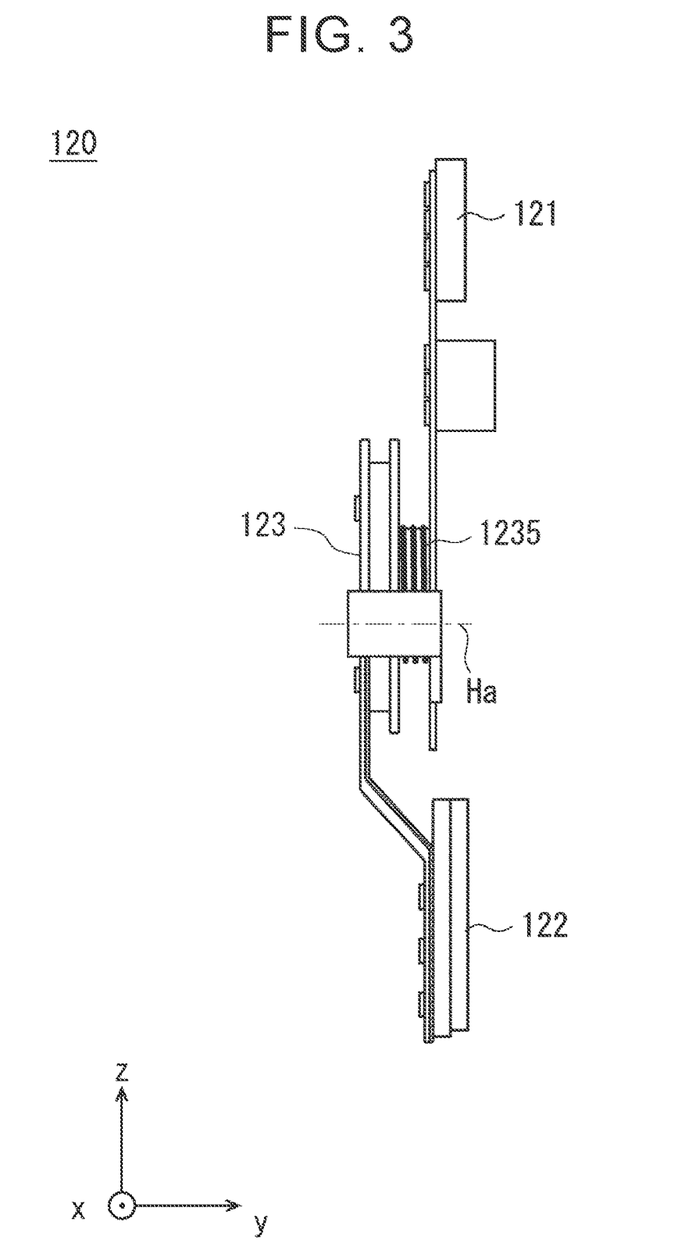
FIG. 3 is a front view showing the configuration of the leg orthosis.
Figure 4:
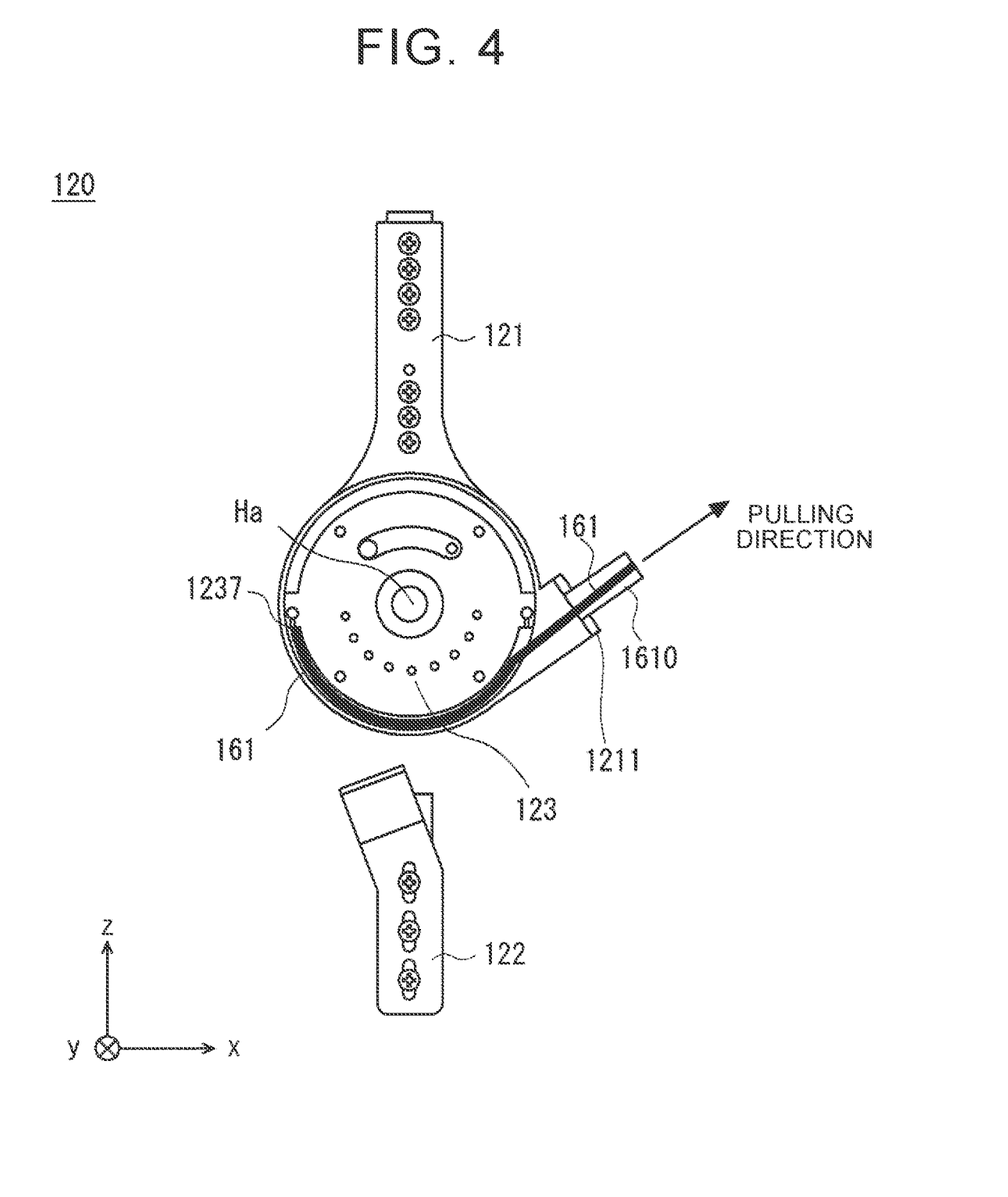
FIG. 4 is a view showing the internal configuration of the leg orthosis.

Next, the leg orthosis 120 will be described, using FIG. 2 to FIG. 4. FIG. 2 to FIG. 4 show one example of the configuration of the leg orthosis 120. FIG. 2 is a side view of the leg orthosis 120, and FIG. 3 is a front view thereof. FIG. 4 is a cross-sectional view showing the internal configuration of a joint mechanism 123.

The leg orthosis 120 includes an upper-leg frame 121, lower-leg frame 122, and the joint mechanism 123. The upper-leg frame 121 is fitted to the upper leg of the impaired leg of the trainee 900. For example, the upper-leg frame 121 is fixed to the upper leg, using a band, hook-and-loop fastener, belt (not shown), or the like. Namely, the band, or the like, that extends from the upper-leg frame 121 is wrapped around the upper leg of the trainee 900, so that the upper-leg frame 121 is placed along the upper leg. The upper-leg frame 121 is provided with an insertion opening 1211 for mounting the wire 161 in position. The insertion opening 1211 is a coupling point of the wire 161 with the leg orthosis 120.

The lower-leg frame 122 is fitted to the lower leg of the trainee 900. For example, the lower-leg frame 122 is fixed to the lower leg, using a band, hook-and-loop fastener, belt (not shown), or the like. Namely, the band, or the like, that extends from the lower-leg frame 122 is wrapped around the lower leg of the trainee 900, so that the lower-leg frame 122 is placed along the lower leg.

The lower-leg frame 122 is connected to the upper-leg frame 121, via the joint mechanism 123. The joint mechanism 123 connects the lower-leg frame 122 with the upper-leg frame 121 such that the lower-leg frame 122 can freely pivot relative to the upper-leg frame 121. The joint mechanism 123 corresponds to the knee joint of the impaired leg. The joint mechanism 123 pivotally connects the upper-leg frame 121 with the lower-leg frame 122. The joint mechanism 123 may have a hinge or a bearing.

The joint mechanism 123 pivots according to the motion of the knee joint of the trainee 900. The joint mechanism 123 changes the angle formed by the upper-leg frame 121 and the lower-leg frame 122 in the direction of extension or flexion of the knee joint. Namely, the lower-leg frame 122 pivots about a joint axis Ha of the joint mechanism 123, relative to the upper-leg frame 121. The trainee wears the leg orthosis 120, in a condition where the leg orthosis 120 is located at one side of the knee joint of the impaired leg. The upper-leg frame 121 and the lower-leg frame 122 pivot about the joint axis Ha. Thus, during walking training, the leg orthosis 120 can assist movement of the knee joint. In this connection, movable ranges of the upper-leg frame 121 and the lower-leg frame 122 may be mechanically restricted by a stopper, for example.

As shown in FIG. 3, the joint mechanism 123 is provided with a biasing member 1235. The biasing member 1235 is a torsion spring, for example, and generates biasing force between the upper-leg frame 121 and the lower-leg frame 122, so that the knee joint extends. Namely, the biasing member 1235 generates biasing force, so that the upper-leg frame 121 and the lower-leg frame 122 extend in parallel with each other.

As shown in FIG. 2 and FIG. 4, the wire 161 is mounted in the joint mechanism 123. For example, the wire 161 is inserted through the insertion opening 1211 of the upper-leg frame 121, into the joint mechanism 123. A distal end of the wire 161 is fixed to a stationary end 1237 of the joint mechanism 123. Also, at the insertion opening 1211, an outer 1610 of the wire 161 is fixed to the upper-leg frame 121.

The first drive mechanism 162 pulls the wire 161, so that the joint mechanism 123 pivots in such a direction as to flex the knee joint. More specifically, as shown in FIG. 2, the wire 161 is pulled in a direction indicated by a straight arrow, so that the length of the wire 161 from the stationary end 1237 to the insertion opening 1211 is reduced. As a result, the stationary end 1237 gets closer to the insertion opening 1211, so that the joint mechanism 123 pivots in the direction to flex the knee joint. Also, when the wire 161 stops being pulled, the joint mechanism 123 pivots in the direction of extension, under the bias force of the biasing member 1235. The leg orthosis 120 can assist extension and flexion of the knee joint, in accordance with the walking motion of the trainee 900.

Thus, it is possible to change the joint angle of the joint mechanism 123, by using the wire 161 from the outside of the leg orthosis 120. Namely, when the pull force of the wire 161 is increased, the joint mechanism 123 is driven in the direction to flex the knee joint. Also, when the pull force of the wire 161 is reduced, the joint mechanism 123 is driven, in the direction to extend the knee joint under the bias force of the biasing member 1235. Thus, the overall controller 210 controls the pull force applied from the first drive mechanism 162 shown in FIG. 1 to the wire 161, according to movement of the knee joint of the trainee 900.

Thus, the movement of the knee joint can be supported, by use of the pull force of the wire 161 connected from the outside to the leg orthosis 120. In other words, the motor and actuator for applying drive force to the leg orthosis 120 can be placed outside the leg orthosis 120. With this arrangement, electric equipment, such as a motor, can be placed outside the leg orthosis. For example, the leg orthosis 120 does not require a motor, and a power supply for driving the motor. Thus, the weight and size of the leg orthosis 120 can be reduced. The joint mechanism 123 may be provided with an angle sensor that detects the angle formed by the upper-leg frame 121 and the lower-leg frame 122.

Figure 5:
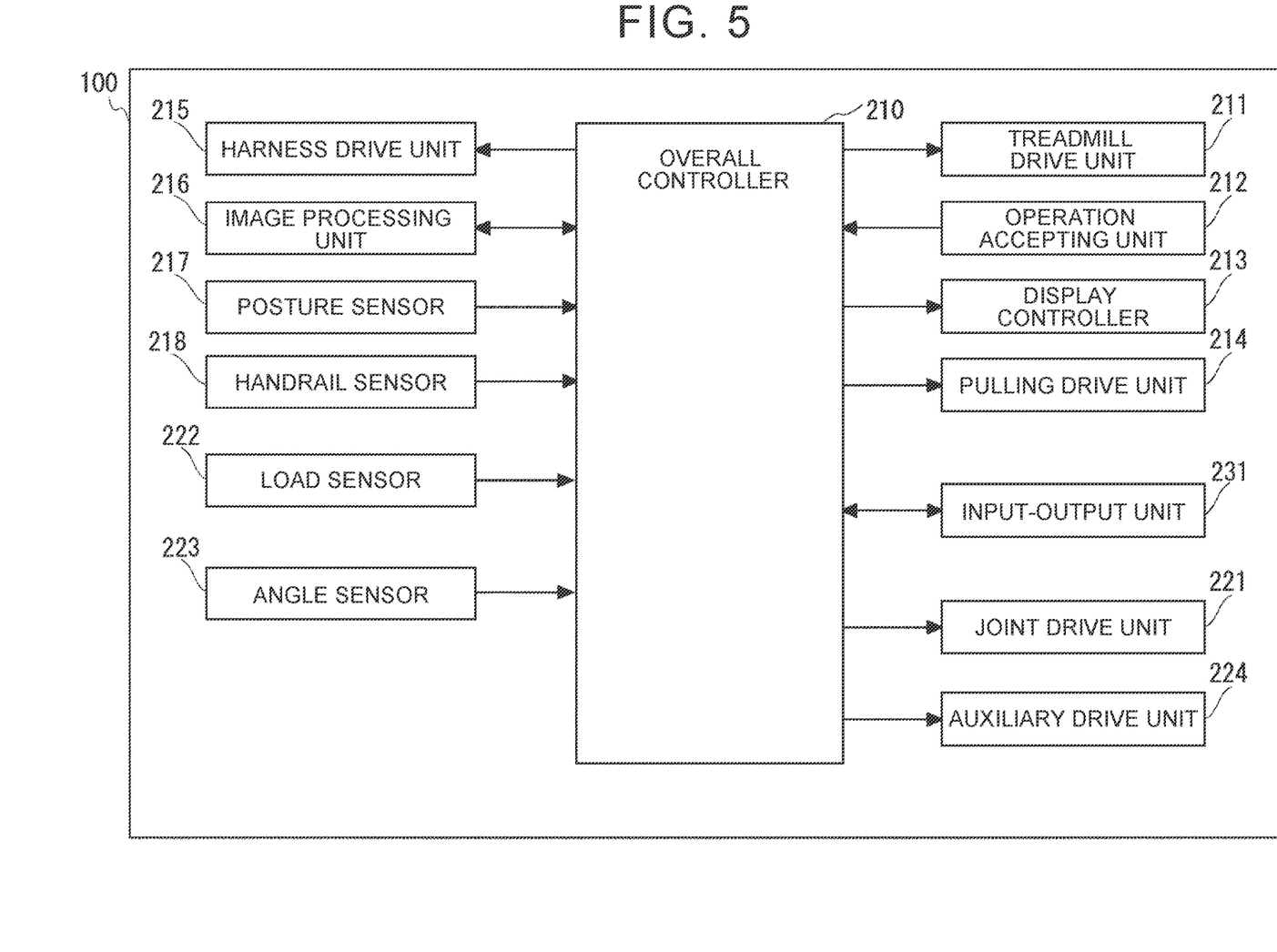
FIG. 5 is a control block diagram showing a control system of the walking training system.

Referring next to FIG. 5, an example of the system configuration of the walking training apparatus 100 will be described. FIG. 5 is a block diagram showing the example of the system configuration of the walking training apparatus 100. As shown in FIG. 5, the walking training apparatus 100 may include the overall controller 210, a treadmill drive unit 211, an operation accepting unit 212, a display controller 213, and a pulling drive unit 214. The walking training apparatus 100 may also include a harness drive unit 215, image processing unit 216, posture sensor 217, handrail sensor 218, communication connection interface (IF), and input-output unit 231. The walking training apparatus 100 includes a joint drive unit 221, load sensor 222, angle sensor 223, and auxiliary drive unit 224.

The overall controller 210 is a Micro Processing Unit (MPU), for example, and executes control programs read from a system memory, to perform control on the apparatus as a whole.

The treadmill drive unit 211 includes a motor that rotates the belt 132, and a drive circuit for the motor. The overall controller 210 sends a drive signal to the treadmill drive unit 211, to control rotation of the belt 132. The overall controller 210 adjusts the rotational speed of the belt 132, according to the walking speed set by the trainer 901, for example.

The operation accepting unit 212 accepts input operation from the trainer 901, and sends an operation signal to the overall controller 210. The trainer 901 operates operation buttons provided on the apparatus, a touch panel superposed on the monitor for management 139, accompanying remote controller, etc. which constitute the operation accepting unit 212. Through the operation, it is possible to turn on/off the power supply, give a command to start training, enter numerical values concerning settings, and select menu items. The operation accepting unit 212 may also accept input operation from the trainee 900.

The display controller 213 receives a display signal from the overall controller 210, generates a display image, and displays the image on the monitor for training 138 or monitor for management 139. The display controller 213 generates an image indicating the progress of training, or a real-time picture taken by the camera 140, according to the display signal.

The pulling drive unit 214 includes a motor for pulling the anterior wire 134 and its drive circuit, which constitute the anterior pulling portion 135, and a motor for pulling the posterior wire 136 and its drive circuit, which constitute the posterior pulling portion 137. The overall controller 210 sends a drive signal to the pulling drive unit 214, to control winding of the anterior wire 134 and winding of the posterior wire 136, respectively. Also, the overall controller 210 controls the pull force of each wire, as well as the winding operation, by controlling drive torque of the motor. The overall controller 210 identifies the time of switching of the impaired leg from a stance phase to a swing phase, from the detection result of the load sensor 222, for example, and increases or reduces the pull force of each wire in synchronization with the switching time, to thus assist swinging motion of the impaired leg.

The harness drive unit 215 includes a motor for pulling the harness wire 111 and its drive circuit, which constitute the harness pulling portion 112. The overall controller 210 sends a drive signal to the harness drive unit 215, to control winding of the harness wire 111 and the pull force of the harness wire 111. When the overall controller 210 predicts a fall of the trainee 900, for example, it reels in the harness wire 111 by a given amount, to prevent the fall of the trainee.

The image processing unit 216 is connected to the camera 140, and can receive an image signal from the camera 140. The image processing unit 216 receives the image signal from the camera 140, according to a command from the overall controller 210, and generates image data by processing the received image signal. Also, the image processing unit 216 performs image processing on the image signal received from the camera 140, according to a command from the overall controller 210, to carry out a particular image analysis. For example, the image processing unit 216 detects a foot position (stance position) of the impaired leg that contacts the treadmill 131, through the image analysis. More specifically, the image processing unit 216 extracts an image area around a tip of the foot or toe, for example, and computes the stance position, by analyzing an identification marker depicted on the belt 132 that overlaps the tip portion.

The posture sensor 217 detects the inclination angle of the abdomen region of the trainee 900 relative to the direction of the gravity, as described above, and sends a detection signal to the overall controller 210. The overall controller 210 computes the posture of the trainee 900, more specifically, the inclination angle of the trunk, using the detection signal from the posture sensor 217. The overall controller 210 and the posture sensor 217 may be connected by wire, or may be wirelessly connected via near-field communication.

The handrail sensor 218 detects a load applied to the handrail 130a. Namely, the load corresponding a part of the body weight of the trainee 900 that cannot be supported by his/her both legs is applied to the handrail 130a. The handrail sensor 218 detects the load, and sends a detection signal to the overall controller 210.

The overall controller 210 also plays a role of a function executing unit that performs various computations concerning control, and controls. The overall controller 210 controls each drive unit, using data obtained from various sensors.

The joint drive unit 221 includes a drive control circuit of the first drive mechanism 162 (see FIG. 1). The joint drive unit 221 generates a drive signal of a take-up motor, according to a control signal from the overall controller 210. The joint drive unit 221 sends the drive signal to the first drive mechanism 162, so that the first drive mechanism 162 reels in or reels out the wire 161. As a result, the upper-leg frame 121 and the lower-leg frame 122 are forced to open relative to each other about the joint axis Ha, or forced to close. With the movements, the extending motion and flexing motion of the knee are assisted, and the knee is prevented from buckling. The joint drive unit 221 drives the first drive mechanism 162, according to the walking motion. It is possible to control the joint mechanism 123 of the leg orthosis 120, according to the knee joint movement of the trainee 900.

The load sensor 222 detects the magnitude and distribution of vertical loads received by the sole of the foot of the trainee 900 as described above, and sends a detection signal to the overall controller 210. The load sensor 222 may be provided on the treadmill 131. When the leg orthosis 120 has a sole frame attached to the sole of the trainee 900, the load sensor 222 may be provided on the sole frame. Also, the load sensor 222 may be attached to a shoe of the trainee 900. The overall controller 210 determines the swing or stance phase, or estimates switching of the phases, based on the detection signal from the load sensor 222.

The angle sensor 223 detects the angle formed by the upper-leg frame 121 and the lower-leg frame 122 about the joint axis Ha as described above, and sends a detection signal to the overall controller 210. The overall controller 210 receives the detection signal, and computes the opening angle of the knee joint. The angle sensor 223 may be provided on the leg orthosis 120, or may be provided on a place other than the leg orthosis 120. For example, a camera that shoots the trainee 900 from one side thereof may be used as the angle sensor 223. In this case, the image processing unit 216, for example, can perform image analysis, and obtain the opening angle of the knee joint.

The auxiliary drive unit 224 includes a drive control circuit of the second drive mechanism 172 (see FIG. 1). The auxiliary drive unit 224 generates a drive signal of a take-up motor, according to a control signal from the overall controller 210. The auxiliary drive unit 224 sends the drive signal to the second drive mechanism 172, so that the second drive mechanism 172 reels in or reels out the holding belt 171. In this manner, the second drive mechanism 172 can control the level of the wire 161.

The auxiliary drive unit 224 drives the second drive mechanism 172, according to the walking motion. For example, the knee height of the trainee 900 varies according to the walking motion. The auxiliary drive unit 224 changes the level of the wire 161 so as to follow the variation in the knee height. In other words, the auxiliary drive unit 224 raises the holding level of the wire 161, at the time when the knee height of the trainee 900 rises. To the contrary, the auxiliary drive unit 224 lowers the holding level of the wire 161, at the time when the knee height of the trainee 900 becomes lower. Thus, the auxiliary drive unit 224 can control the level of the wire 161, according to the trajectory of the knee joint of the trainee 900.

The overall controller 210 detects the walking motion of the trainee 900. The overall controller 210 detects the walking motion with various sensors, such as the angle sensor 223, load sensor 222, and posture sensor 217. Then, the overall controller 210 controls the first drive mechanism 162 and the second drive mechanism 172, according to the walking motion of the trainee 900. The overall controller 210 detects the time of switching between the swing phase and the stance phase in a walking motion, take-off time, landing time, etc., according to detection signals from various sensors. The sensors for detecting the phase and timing of walking motion are not limited to any particular ones, since known methods can be used.

The overall controller 210 controls the first drive mechanism 162 and the second drive mechanism 172, according to the walking motion. The overall controller 210 generates a control signal for each drive unit, according to the phase of the walking motion. The overall controller 210 outputs control signals to the auxiliary drive unit 224, joint drive unit 221, pulling drive unit 214, and harness drive unit 215. The auxiliary drive unit 224, joint drive unit 221, pulling drive unit 214, and harness drive unit 215 drive the corresponding motors, etc. For example, drive patterns corresponding to the respective phases and timing of walking motion may be registered. Then, the overall controller 210 generates control signals corresponding to the drive patterns. The drive pattern may also reflect body information, such as the height, weight, leg length, upper-leg length, and lower-leg length, of the trainee 900.

Figure 6:
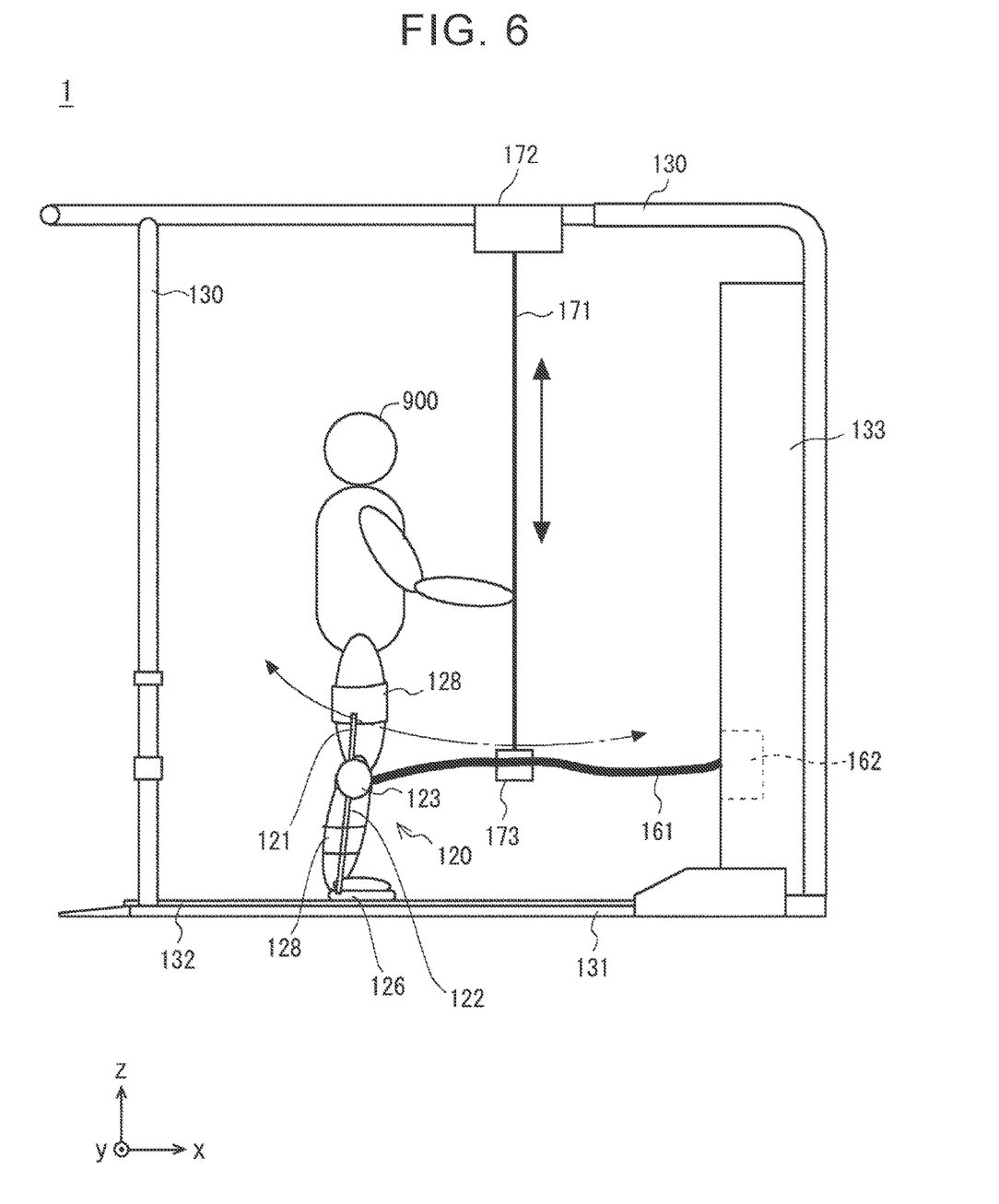
FIG. 6 is a schematic view showing a main arrangement for driving the leg orthosis.

Referring to FIG. 6, driving of the leg orthosis 120 will be described. FIG. 6 is a side view schematically showing the walking training system. In FIG. 6, the configuration shown in FIG. 1 is simplified as appropriate. More specifically, FIG. 6 indicates the configuration related to the leg orthosis 120 and its driving. For example, in FIG. 6, the harness wire 111, harness pulling portion 112, handrails 130a, anterior wire 134, anterior pulling portion 135, posterior wire 136, posterior pulling portion 137, etc., are not illustrated.

The leg orthosis 120 is fitted to the right leg of the trainee 900. More specifically, the upper-leg frame 121 and the lower-leg frame 122 are attached to the upper leg and lower leg of the right leg, respectively, with bands 128. Namely, the band 128 is wrapped around the upper leg, so that the upper-leg frame 121 is fixed along the upper leg. Similarly, the band 128 is wrapped around the lower leg, so that the lower-leg frame 122 is fixed along the lower leg. The upper-leg frame 121 and the lower-leg frame 122 are pivotally connected via the joint mechanism 123.

Further, a sole frame 126 is attached to the lower end of the lower-leg frame 122. The trainee 900 places the right leg on the sole frame 126. The sole frame 126 is in contact with the belt 132 of the treadmill 131. The sole frame 126 may be provided with the load sensor 222 as described above. Needless to say, when the impaired leg of the trainee 900 is the left leg, the trainee 900 may wear the leg orthosis 120 on the left leg.

The wire 161 is connected to the joint mechanism 123. The wire 161 connects the first drive mechanism 162 with the joint mechanism 123. The first drive mechanism 162 reels in the wire 161, so that the pull force is applied to the wire 161. As a result, the angle of the joint mechanism 123 changes. Thus, the leg orthosis 120 can assist movement of the knee joint, according to the walking motion.

The first drive mechanism 162 is located outside the leg orthosis 120. The first drive mechanism 162 can apply force for assisting movement of the knee joint, from the outside of the leg orthosis 120. Thus, the leg orthosis 120 does not need to incorporate a motor, power supply, etc. Thus, the weight and size of the leg orthosis 120 can be reduced.

Further, the holding belt 171 can be located so as not to interfere with the trainee 900 in walking training. For example, the holding belt 171 is located ahead of the trainee 900. The first drive mechanism 162 and the second drive mechanism 172 may also be located so as not to interfere with the trainee 900. For example, the second drive mechanism 172 is located above the trainee 900, and the first drive mechanism 162 is located ahead of the trainee 900 and the holding belt 171. Thus, the trainee 900 can conduct walking training, without interfering with each drive mechanism, etc.

The wire 161 is made thicker, so as to increase drive torque of the joint mechanism 123. For example, the diameter of the wire 161 is made equal to 15 mm, so that sufficient pull force is applied to the joint mechanism 123. As the weight of the wire 161 increases, the wire 161 becomes less likely to bend. When the knee joint of the trainee 900 moves, the wire 161 may give resistance that impedes movement of the trainee 900. Since the second drive mechanism 172 changes the holding level of the holding belt 171, the wire 161 is prevented from impeding movement of the trainee 900. Also, there is a possibility of an abrupt bend in the wire 161, from the joint mechanism 123 toward the ground. With the holding belt 171 keeping the level of the wire 161, as in this embodiment, the abrupt bend of the wire 161 can be prevented.

When the first drive mechanism 162 is located ahead of the treadmill 131, the length of the wire 161 is increased. In this case, the wire 161 may be brought into contact with the ground, owing to deflection of the wire 161 due to its self-weight. However, the wire 161 can be prevented from contacting with the ground, since the holding belt 171 keeps the level of the wire 161.

It is preferable to keep a predetermined distance from a coupling position of the wire 161 and the leg orthosis 120, to the joint mechanism 123, so as to prevent unnecessary pull force from being applied to the joint mechanism 123. The wire 161 is preferably pulled around at right angles with respect to the upper leg. In this case, the wire 161 and the connecting portion 173 are preferably designed with a certain degree of freedom in the lateral direction. Namely, a mechanism for moving the wire 161 and the connecting portion 173 in the lateral direction according to the walking motion may be provided.

It is preferable that the wire 161 is connected to the leg orthosis 120, from the front side of the trainee 900. With this arrangement, the wire 161 is prevented from interfering with the trainer 901 and other configurations. With this arrangement, the trainer 901 can help the trainee 900 from behind. Also, even when the handrail 130*a* is present at one side of the trainee 900, the wire 161 can be pulled around without interfering with the handrail 130*a*.

By pulling the wire 161 around from the front side, the pull-around direction of the wire 161 can be made in parallel with or close to the horizontal direction. With the wire 161 thus pulled around horizontally, the wire 161 can be prevented from interfering with the arm of the trainee 900. It is preferable to apply pull force in a direction perpendicular to the upper leg. The wire 161 is pulled around from the front in the horizontal direction, to be connected to the leg orthosis 120. The first drive mechanism 162 is preferably located at around the knee height in front of and ahead of the trainee 900.

Figure 7:
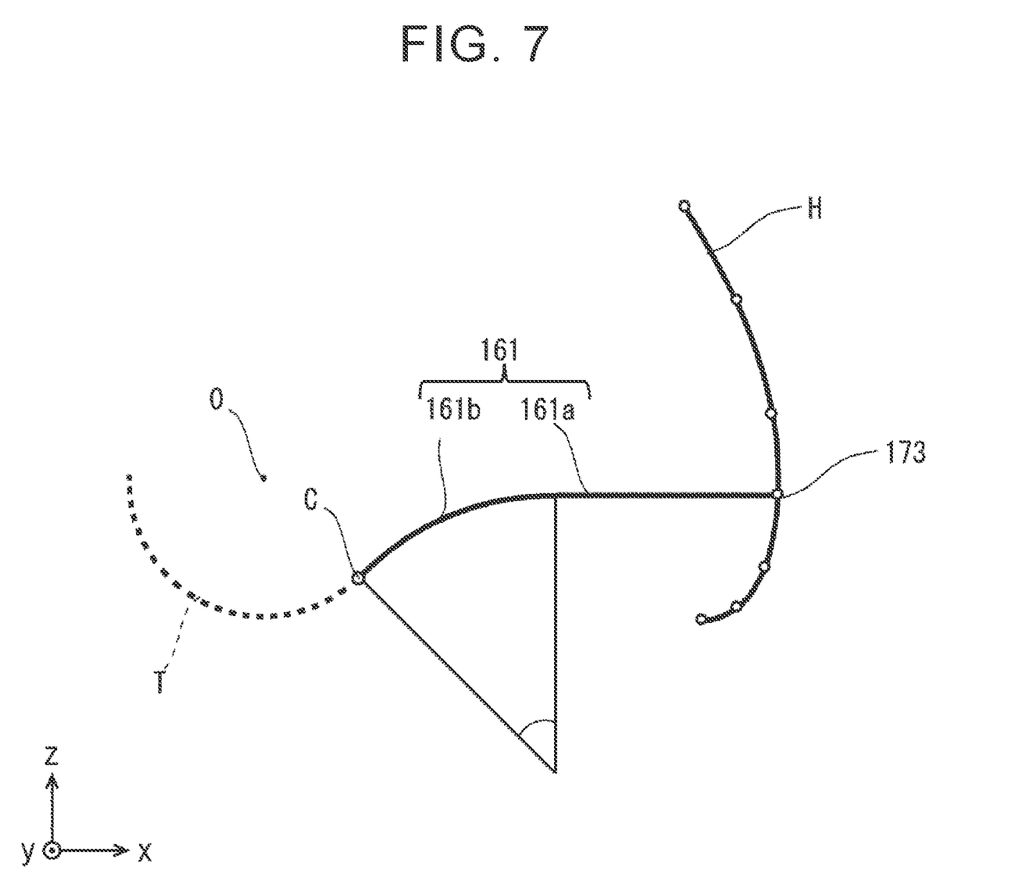
FIG. 7 is a schematic view showing the trajectory of a knee joint.

FIG. 7 is a side view schematically showing the result obtained by calculating the trajectory of the knee joint of the trainee 900. In FIG. 7, the distance from the hip joint to the knee joint of the trainee is assumed to be 50 cm. Accordingly, the trajectory T of the knee joint is a circular arc having a center O, and a radius of 50 cm. Namely, in walking motion, the position of the knee joint relative to the hip joint changes along a track of the arc having the radius of 50 cm.

The minimum bending radius of the wire 161 is assumed to be 100 cm, and the remaining portion extends horizontally. Thus, the wire 161 is divided into a straight portion 161*a* and an arc portion 161*b*. The arc portion 161*b* is a portion closer to the distal end of the wire 161, namely, closer to the leg orthosis 120. The straight portion 161*a* is provided on the first drive mechanism 162 side (not shown in FIG. 7), and extends in parallel with the X direction.

At this time, it is desirable that the wire 161 is connected at right angles with the upper leg; therefore, the trajectory T of the knee joint is connected to the arc portion 161*b* of the wire 161 with a tangent line. The arc portion 161*b* and the trajectory T are smoothly connected, at the coupling portion C of the wire 161 and the leg orthosis 120. The trajectory of the optimum holding level of the connecting portion 173 in this case is indicated as "trajectory H". Thus, the second drive mechanism 172 may change the level of the connecting portion 173, so that it follows the trajectory H.

In the above description, the wire 161 is used, as the pulling member that applies pull force to the joint mechanism 123 of the leg orthosis 120. The pull member is not limited to the wire 161, but may be a rope, string, band, belt, etc. The pull member may be formed of a material, such as metal, resin, or fiber. The holding belt 171 can keep the holding level, even if the pulling member is made of a material that deflects due to the self-weight, for example.

Similarly, the holding device that holds the wire 161 at a given level is not limited to the holding belt 171. The holding device is not limited to the belt, but may be a wire, rope, string, or band. The holding device may be made of a material, such as metal, resin, or fiber. The holding device is preferably a suspended member that is suspended from above. With this arrangement, the pull force that pulls the suspended member upward can be applied to the suspended member, by means of a motor and a take-up mechanism, for example. The second drive mechanism 172 reels in the suspended member, thereby to apply pull force to pull the suspended member upward. Thus, the holding level can be controlled with a simple arrangement. Further, the XY position of the holding belt 171 may be changed, according to the walking motion.

Also, the joint assisted by the leg orthosis 120 is not limited to the knee joint. For example, the leg orthosis 120 may assist the hop joint or the ankle joint in joint motion. The leg orthosis 120 may assist in two or more joint motions. In this case, two or more wires 161 and two or more drive mechanisms may be provided, depending on the number of the joints to be assisted.

First Modified Example

Figure 8:
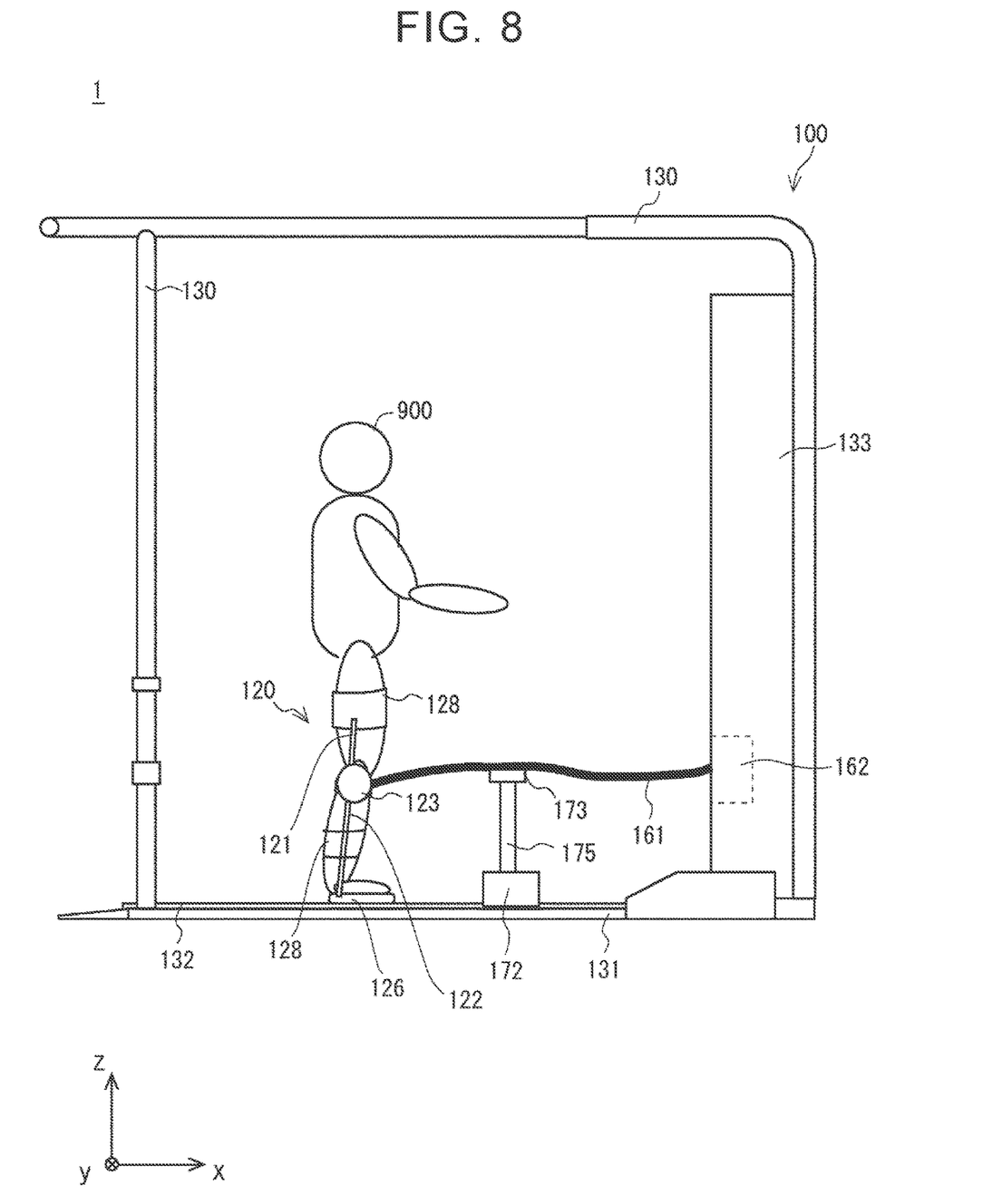
FIG. 8 is a schematic view showing the main configuration of a walking training system according to a first modified example.

The system configuration according to a first modified example will be described with reference to FIG. 8. In the first modified example, the holding device that holds the wire 161 at a holding level is different from that of the above embodiment. Here, a support member 175 holds the wire 161 at a given level.

The support member 175 extends upward from the floor. The support member 175 is able to extend and contract. The upper end of the support member 175 provides a connecting portion 173 that connects with the wire 161. For example, the wire 161 is fixed to the upper face of the support member 175. The second drive mechanism 172 has a motor and a cylinder for extending and contracting the support member 175. The second drive mechanism 172 extends or contracts the support member 175, so that the level of the connecting portion 173 changes. Namely, when the support member 175 extends or contracts, the holding level of the wire 161 changes. With this configuration, too, substantially the same effects as those of the first embodiment can be obtained.

Second Modified Example

Figure 9:
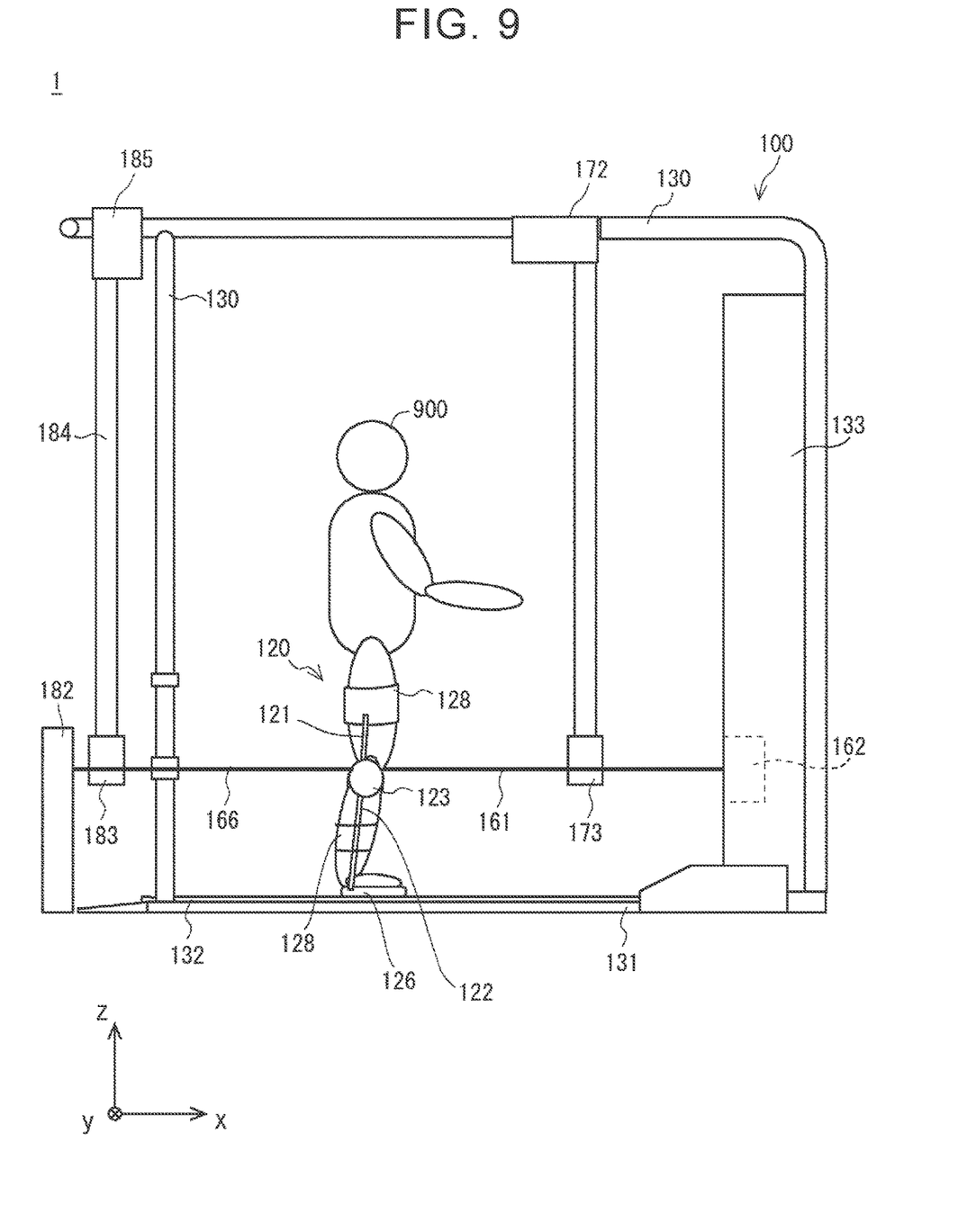
FIG. 9 is a schematic view showing the main configuration of a walking training system according to a second modified example.

The system configuration according to a second modified example will be described with reference to FIG. 9. In the second modified example, a wire 166, third drive mechanism 182, connecting portion 183, holding belt 184, and fourth drive mechanism 185 are provided, in addition to the configuration of FIG. 6. Namely, two wires 161, 166 are connected to the leg orthosis 120. The arrangement associated with the wire 161 is similar to that of the first embodiment, and will not be described in detail. Namely, the first drive mechanism 162 applies pull force to the wire 161, so that the joint mechanism 123 moves in a direction to flex the knee joint.

The wire 166 is connected to the leg orthosis 120 from the rear side. The wire 166 is connected to the third drive mechanism 182. The third drive mechanism 182 is located behind the treadmill 131. The third drive mechanism 182 includes a motor and a take-up mechanism, like the first drive mechanism 162.

The third drive mechanism 182 can apply pull force to the leg orthosis 120, by reeling in the wire 166. The third drive mechanism 182 can weaken the pull force applied to the leg orthosis 120, by reeling out the wire 166. In this manner, the joint portion of the leg orthosis 120 is driven. In other words, the third drive mechanism 182 drives the wire 166, so that the angle of the joint portion of the leg orthosis 120 becomes equal to a desired angle.

In the connecting portion 183, the wire 166 is connected to the holding belt 184. Namely, the holding belt 184 holds the wire 166 via the connecting portion 183. The holding belt 184 holds the wire 166 so that the level of the wire 166 becomes equal to a given level.

The holding belt 184 is attached to the fourth drive mechanism 185. The fourth drive mechanism 185 has a motor and a take-up mechanism, like the second drive mechanism 172. Thus, the fourth drive mechanism 185 can change the holding level of the wire 166, by reeling in or reeling out the holding belt 184.

The two or more wires 161, 166 are connected to the leg orthosis 120 from different directions. The pull force provided by the first drive mechanism 162 and the pull force provided by the third drive mechanism 182 can be applied in different directions. The pull force is applied forward from the wire 161 to the leg orthosis 120, and the pull force is applied backward from the wire 166 to the leg orthosis 120. With the two wires 161, 166 thus provided, the joint mechanism 123 can be pushed and pulled. With this arrangement, the pull force can be applied both forward and backward. Thus, two or more wires are connected to the leg orthosis 120, so that the pull force can be applied in two or more directions.

Furthermore, the drive direction of the joint mechanism 123 can be varied, with the pull force provided by the first drive mechanism 162 and the pull force provided by the third drive mechanism 182. For example, the joint mechanism 123 moves in the direction to extend the knee joint, due to the pull force of the third drive mechanism 182. The joint mechanism 123 moves in the direction to flex the knee joint, due to the pull force of the first drive mechanism 162. Thus, the angle of the knee joint can be quickly made equal to a desired angle; therefore, the motion of the knee joint can be supported more appropriately.

Third Modified Example

Figure 10:
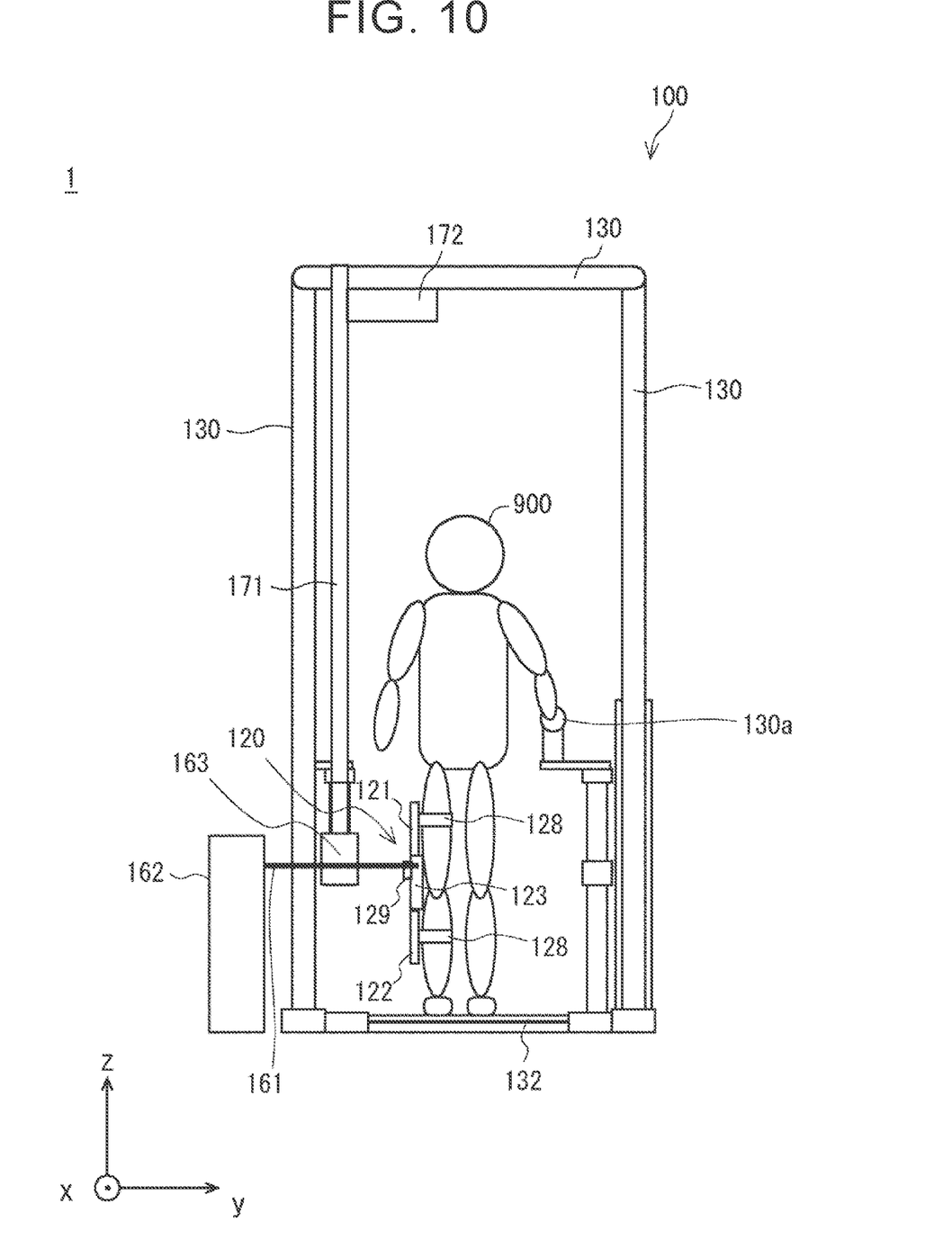
FIG. 10 is a schematic view showing the main configuration of a walking training system according to a third modified example.

In a third modified example, the wire 161 is pulled around from one side of the trainee 900, as shown in FIG. 10. More specifically, the wire 161 is connected to the leg orthosis 120 from the −Y side. A distal end of the wire 161 is connected to the leg orthosis 120, and the other end is connected to the first drive mechanism 162. Then, the first drive mechanism 162 reels in the wire 161, so that pull force is applied to the leg orthosis 120. In this manner, the joint mechanism 123 is driven.

The holding belt 171 holds the wire 161. The holding belt 171 is connected to the wire 161 at a point on the wire 161. The holding belt 171 and the wire 161 are connected via the connecting portion 173. With this arrangement, the second drive mechanism 172 can raise and lower the holding level of the wire 161, according to the walking motion.

Further, the leg orthosis 120 is provided with a shifting mechanism 129 that changes the direction of pull force. The shifting mechanism 129 has a pulley, for example. Then, the shifting mechanism 129 changes the direction of the wire 161 provided along the lateral direction. More specifically, when the direction of the wire 161 is changed by 90°, the pull force can be applied from ahead of the leg orthosis 120. In this manner, the first drive mechanism 162 can pull the wire 161 in the lateral direction.

The operation method of the walking training system can be implemented by a computer program or hardware. The overall controller 210 includes a memory that stores the program, and a processor, etc. that executes the program. The overall controller 210 can implement the operation method of the walking training system 1 according to this embodiment, by executing the program.

The program as described above may be stored and supplied to a computer, using any of various types of non-transitory computer-readable media. The non-transitory computer-readable media include various types of tangible recording media. Examples of the non-transitory computer-readable media include a magnetic recording media (e.g., a flexible disc, magnetic tape, hard disc drive), magneto-optical recording medium (e.g., magneto-optical disc), CD-ROM (Read Only Memory), CD-R, CD-R/W, and semiconductor memory (e.g., mask ROM, PROM (Programmable ROM), EPROM (Erasable PROM), flash ROM, RAM (Random Access Memory)). Also, the program may be supplied to the computer, via any of various types of transitory computer-readable media. Example of the transitory computer-readable media include an electric signal, optical signal, and electromagnetic wave. The transitory computer-readable medium can supply the program to the computer, via a wire communication channel, such as an electric wire or an optical fiber, or a wireless communication channel.

The disclosure is not limited to the above embodiment, but may be changed as appropriate, without departing from the principle.

What is claimed is:
1. A walking training system comprising:
a leg orthosis configured to fit to a leg of a user;
at least one pulling member coupled to the leg orthosis;
a first drive mechanism configured to apply pull force to the at least one pulling member, according to a walking motion of the user;
a holding device that holds the at least one pulling member at a holding level, the holding device attached to the at least one pulling member at a location of the at least one pulling member that is between (a) a coupling point at which the at least one pulling member is attached to the leg orthosis and (b) the first drive mechanism;
a second drive mechanism configured to change the holding level of the at least one pulling member held by the holding device, according to the walking motion of the user; and
a controller configured to control the first drive mechanism and the second drive mechanism, wherein:
the leg orthosis includes (i) an upper frame configured to be attached to the leg of the user above a knee of the user, (ii) a lower frame configured to be attached to the leg of the user below the knee of the user, and (iii) a joint mechanism that pivotally connects the upper frame to the lower frame and is configured to pivot according to the walking motion of the user,
the at least one pulling member is connected to the joint mechanism,
the first drive mechanism is configured to pivot the joint mechanism by pulling the at least one pulling member under control of the controller, and
the second drive mechanism is configured to change the holding level of the at least one pulling member to follow a height of the joint mechanism which changes as the joint mechanism pivots, so that the holding level rises as the joint mechanism rises and the holding level lowers as the joint mechanism lowers due to pivoting of the joint mechanism.

2. The walking training system according to claim 1, wherein:
the at least one pulling member is coupled to the leg orthosis from ahead of the user; and
the first drive mechanism is configured to provide the pull force, by reeling in the at least one pulling member under control of the controller.

3. The walking training system according to claim 1, wherein:
the holding device has a suspended member that is suspended from above the user; and
the second drive mechanism is configured to raise the holding level, by reeling in the suspended member under control of the controller.

4. The walking training system according to claim 1, wherein:
the holding device has a support member that extends upward; and
the second drive mechanism is configured to change the holding level, by extending and contracting the support member under control of the controller.

5. The walking training system according to claim 1, wherein the at least one pulling member is a plurality of pulling members, and the plurality of pulling members is connected to the leg orthosis from different directions.

6. The walking training system according to claim 1, wherein:
the at least one pulling member is coupled to the leg orthosis from one side of the user; and
the leg orthosis is provided with a mechanism configured to change a direction of the pull force of the pulling member.

7. The walking training system according to claim 1, wherein:
the first drive mechanism is configured to drive the at least one pulling member so that an angle of the joint mechanism becomes equal to a determined angle.

8. The walking training system according to claim 1, further comprising:
a harness configured to be attached to the user separately from the orthosis, the harness including a posture sensor configured to detect a posture of the user, wherein
the controller controls the first drive mechanism and the second drive mechanism based on a detection result of the posture sensor.

9. The walking training system according to claim 1, wherein:
the at least one pulling member is inserted into the joint mechanism.

10. An operation method of a walking training system including (i) a leg orthosis configured to fit to a leg of a user, (ii) at least one pulling member coupled to the leg orthosis, (iii) a first drive mechanism configured to apply pull force to the at least one pulling member, (iv) a holding device that holds the at least one pulling member at a holding level, the holding device attached to the at least one pulling member at a location of the at least one pulling member that is between (a) a coupling point at which the at least one pulling member is attached to the leg orthosis and (b) the first drive mechanism, (v) a second drive mechanism configured to change the holding level of the at least one pulling member held by the holding device, and (vi) a controller configured to control the first drive mechanism and the second drive mechanism, (A) the leg orthosis including (1) an upper frame configured to be attached to the leg of the user above a knee of the user, (2) a lower frame configured to be attached to the leg of the user below the knee of the user, and (3) a joint mechanism that pivotally connects the upper frame to the lower frame and is configured to pivot according to a walking motion of the user, and (B) the at least one pulling member is connected to the joint mechanism, the operation method comprising:
detecting the walking motion of the user; and
controlling the first drive mechanism and the second drive mechanism by the controller, according to the walking motion of the user, wherein
the controller controls the first drive mechanism to pivot the joint mechanism by pulling the at least one pulling member, and
the controller controls the second drive mechanism to change the holding level of the at least one pulling member to follow a height of the joint mechanism which changes as the joint mechanism pivots, so that the holding level rises as the joint mechanism rises and the holding level lowers as the joint mechanism lowers due to pivoting of the joint mechanism.

11. A non-transitory storage medium for a walking training system including (i) a leg orthosis configured to fit to a leg of a user, (ii) at least one pulling member coupled to the leg orthosis, (iii) a first drive mechanism configured to apply pull force to the at least one pulling member, (iv) a holding device that holds the at least one pulling member at a holding level, the holding device attached to the at least one pulling member at a location of the at least one pulling member that is between (a) a coupling point at which the at least one pulling member is attached to the leg orthosis and (b) the first drive mechanism, and (v) a second drive mechanism configured to change the holding level of the at least one pulling member held by the holding device, (A) the leg orthosis including (1) an upper frame configured to be attached to the leg of the user above a knee of the user, (2) a lower frame configured to be attached to the leg of the user below the knee of the user, and (3) a joint mechanism that pivotally connects the upper frame to the lower frame and is configured to pivot according to a walking motion of the user, and (B) the at least one pulling member is connected to the joint mechanism,
wherein the non-transitory storage medium stores instructions that are executable by one or more processors and that cause the one or more processors to perform functions comprising:
detecting the walking motion of the user; and
controlling the first drive mechanism and the second drive mechanism by the one or more processors, according to the walking motion of the user that has been detected, wherein
the one or more processors control the first drive mechanism to pivot the joint mechanism by pulling the at least one pulling member, and
the one or more processors control the second drive mechanism to change the holding level of the at least one pulling member to follow a height of the joint mechanism which changes as the joint mechanism pivots, so that the holding level rises as the joint mechanism rises and the holding level lowers as the joint mechanism lowers due to pivoting of the joint mechanism.

* * * * *